(12) United States Patent
Newton

(10) Patent No.: US 10,850,014 B2
(45) Date of Patent: Dec. 1, 2020

(54) LIQUID COLLECTION DEVICE AND METHOD

(71) Applicant: PureWick Corporation, El Cajon, CA (US)

(72) Inventor: Camille Rose Newton, Bonsall, CA (US)

(73) Assignee: PUREWICK CORPORATION, Spring Valley, CA (US)

( * ) Notice: Subject to any disclaimer, the term of this patent is extended or adjusted under 35 U.S.C. 154(b) by 0 days.

(21) Appl. No.: 14/722,613

(22) Filed: May 27, 2015

(65) Prior Publication Data

US 2017/0312405 A1    Nov. 2, 2017

Related U.S. Application Data

(63) Continuation of application No. 62/007,026, filed on Jun. 3, 2014.

(51) Int. Cl.
| | | |
|---|---|---|
| *A61M 1/00* | (2006.01) | |
| *A61F 13/00* | (2006.01) | |
| *A61M 27/00* | (2006.01) | |
| *A61F 13/15* | (2006.01) | |

(52) U.S. Cl.
CPC ..... *A61M 1/0088* (2013.01); *A61F 13/00068* (2013.01); *A61F 13/15* (2013.01); *A61M 1/008* (2013.01); *A61M 1/0023* (2013.01); *A61M 27/00* (2013.01)

(58) Field of Classification Search
CPC .......................... A61M 1/0088; A61F 13/00068

USPC ........................................................ 604/319
See application file for complete search history.

(56) References Cited

U.S. PATENT DOCUMENTS

| | | | | |
|---|---|---|---|---|
| 3,349,768 A | * | 10/1967 | Keane ..................... | A61F 5/455 604/329 |
| 5,636,643 A | | 6/1997 | Argenta et al. | |
| 5,678,564 A | * | 10/1997 | Lawrence ............... | A61F 5/455 600/573 |
| 7,520,872 B2 | * | 4/2009 | Biggie ................ | A61M 1/0088 601/6 |

(Continued)

OTHER PUBLICATIONS

U.S. Appl. No. 62/007,026 filed Jun. 3, 2014.

*Primary Examiner* — Andrew J Mensh
(74) *Attorney, Agent, or Firm* — Dorsey & Whitney LLP

(57) ABSTRACT

A liquid collection device for use in drawing liquid from an opening in a body of a person or an animal. The device includes a perforated container, and an outlet port. The perforated container defines a chamber shaped to collect liquid drawn into the chamber through perforations in the container. The outlet port enables liquid to be drawn from the chamber by a partial vacuum applied at the outlet port. The container is configured to receive wicking material that covers at least some of the perforations and is also configured and dimensioned for placement of the wicking material in, or over approximately an exposed breadth of, an opening in a person or an animal, so that upon said placement of the container with at least some of the perforations being covered by said wicking material, when a partial vacuum is applied at the outlet port, liquid can be drawn from said opening through the wicking material and into the chamber and from the chamber through the outlet port.

6 Claims, 1 Drawing Sheet

(56) References Cited

U.S. PATENT DOCUMENTS

| | | | |
|---|---|---|---|
| 7,699,831 B2* | 4/2010 | Bengtson | A61M 1/0088 |
| | | | 604/313 |
| 2005/0197639 A1* | 9/2005 | Mombrinie | A47L 7/0042 |
| | | | 604/317 |
| 2013/0190706 A1* | 7/2013 | Kleiner | A61F 13/00021 |
| | | | 604/319 |

* cited by examiner

LIQUID COLLECTION DEVICE AND METHOD

CROSS-REFERENCE TO RELATED APPLICATION

This application is a continuation of U.S. Provisional Patent Application No. 62/007,026 filed Jun. 3, 2014.

BACKGROUND OF THE INVENTION

The present invention pertains to collecting liquid and is particularly directed to drawing liquid away from openings in the body of a person or an animal, such as drawing blood away from a wound to the exposed surface portion of the body or from an opening made in the body to facilitate surgery.

Examples of apparatus for drawing liquid away from openings in the body of a person or an animal are described in U.S. Pat. Nos. 5,636,643; 5,678,564 and 7,699,831.

SUMMARY OF THE INVENTION

The invention provides a liquid collection device for use in drawing liquid from an opening in a body of a person or an animal, comprising: a perforated container defining a chamber shaped to collect liquid drawn into the chamber through perforations in the container; wherein the container includes an outlet port through which liquid can be drawn from the chamber by a partial vacuum applied at the outlet port; wherein the container is configured to receive wicking material that covers at least some of the perforations and is also configured and dimensioned for placement of the wicking material in, or over approximately an exposed breadth of, an opening in a person or an animal, so that upon said placement of the container with at least some of the perforations being covered by said wicking material, when a partial vacuum is applied at the outlet port, liquid can be drawn from said opening through the wicking material and into the chamber and from the chamber through the outlet port.

The invention also provides a method of drawing liquid from an opening in a body of a person or an animal, comprising the steps of:

(a) providing a liquid collection that comprises: a perforated container defining a chamber shaped to collect liquid drawn into the chamber through perforations in the container; wherein the container includes an outlet port through which liquid can be drawn from the chamber by a partial vacuum applied at the outlet port; wherein the container is configured to receive wicking material that covers at least some of the perforations and is also configured and dimensioned for placement of the wicking material in, or over approximately an exposed breadth of, an opening in a person or an animal, so that upon said placement of the container with at least some of the perforations being covered by said wicking material, when a partial vacuum is applied at the outlet port, liquid can be drawn from said opening through the wicking material and into the chamber and from the chamber through the outlet port;

(b) covering at least some of the perforations with wicking material;

(c) so placing the container in, or over approximately an exposed breadth of, an opening in a body of a person or an animal that the wicking material is disposed in, or over approximately the exposed breadth of the opening; and (d) applying a partial vacuum at the outlet port to cause liquid to be drawn from the opening through the wicking material and into the chamber and from the chamber through the outlet port.

Thus, the invention provides a liquid collection device and method that both facilitates the use of wicking material to collect liquid from artificial cavities in the body of a person or an animal, and enables transportation of the collected liquid from the device.

Additional features of the invention are described with reference to the detailed description.

These figures are not drawn to scale.

DETAILED DESCRIPTION

Referring to FIGS. 1A, 1B, 1C and 3, one embodiment of a liquid collection device 10 according to the invention is configured and dimensioned for placement of wicking material in an opening in a person or an animal.

The liquid collection device 10 includes a perforated container 12 defining a chamber 14 shaped to collect liquid drawn into the chamber 14 through perforations 16 in the container 12.

Figure 1A:
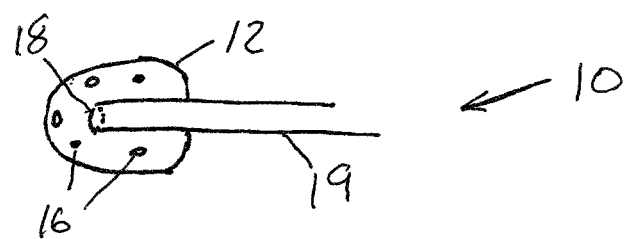
FIGS. 1A, 1B and 1C are views of alternative exemplary embodiments of a liquid collection device configured and dimensioned for one particular use of the invention.
Figure 1B:
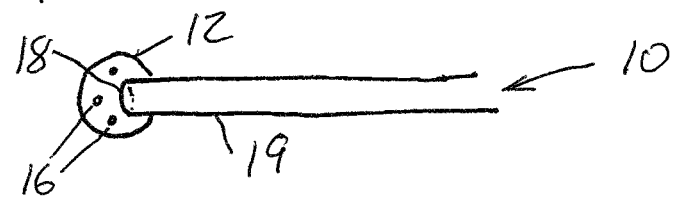
Figure 1C:
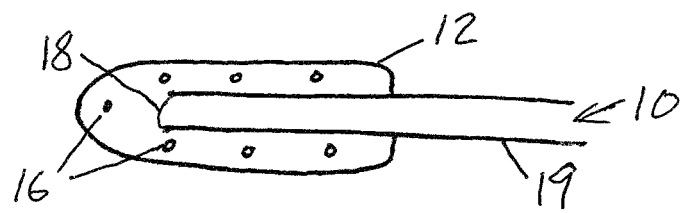

The container 12 can be of various shapes and sizes, as shown in FIGS. 1A, 1B and 1C. In other examples (not shown), the container 12 may have dimensions similar to a thimble. Other examples may be the size of a finger, a fist, or even larger. The container can be round, flat, oblong, square, elongated or not.

The container 12 includes an outlet port 18 through which liquid can be drawn from the chamber 14 by a partial vacuum applied at the outlet port 18 when the chamber 14 is otherwise sealed. Tubing 19 can be connected to the outlet port 18 to facilitate provision of a partial vacuum at the outlet port 18 and transportation of the fluid from the chamber 14.

The container 12 is configured to receive wicking material (not shown) that covers at least some of the perforations 16 and is also configured and dimensioned for placement in an opening in a person or an animal so that upon said placement of the container 12, when a partial vacuum is applied at the outlet port 18, liquid can be drawn from the opening through the wicking material and the perforations 16 and into the chamber 14 and from the chamber 14 through the outlet port 18. Examples of useful wicking material include paper, gauze, or other natural or synthetic material having the ability to wick liquid.

In the embodiment described with reference to FIGS. 1A, 1B, 1C, it is preferable that the perforations 16 are arrayed around the container 12.

When the container 12 is immersed in a wound, the liquid in the opening and the walls of the wound create a seal around the container 12, and thereby enhance the partial vacuum within the container 12.

Figure 2A:
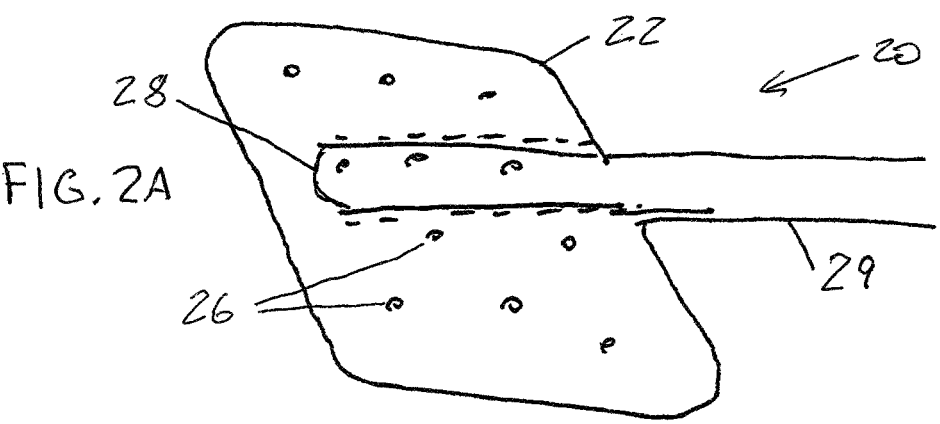
FIGS. 2A and 2B are views of alternative exemplary embodiments of a liquid collection device configured and dimensioned for another particular use of the invention.
Figure 2B:
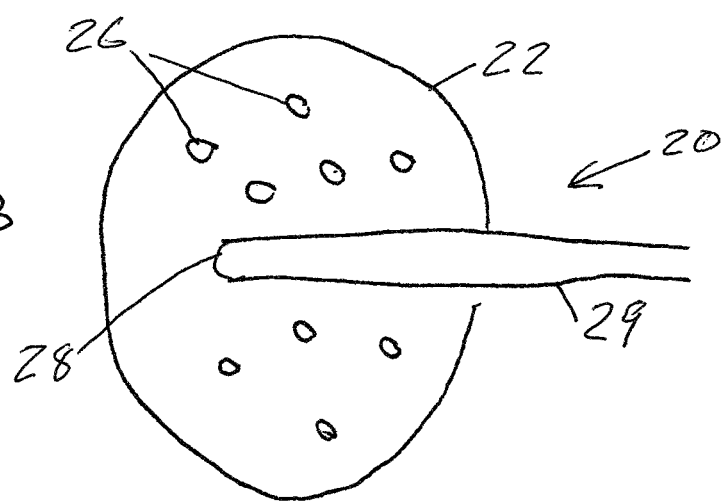
Figure 3:
FIG. 3 illustrates an exemplary profile of a liquid collection device according to the invention.

Referring to FIGS. 2A, 2B and 3, another embodiment of a liquid collection device 20 according to the invention is configured and dimensioned for placement of wicking material over approximately the exposed breadth of an opening in a person or an animal.

The liquid collection device 20 includes a perforated container 22 defining a chamber 14 shaped to collect liquid drawn into the chamber 14 through perforations 26 in the container 22. The container 22 includes an outlet port 28 through which liquid can be drawn from the chamber 14 by a partial vacuum applied at the outlet port 28. Tubing 29 can be connected to the outlet port 28 to facilitate provision of a partial vacuum at the outlet port 28 and transportation of the fluid from the chamber 14.

The container 22 is configured to receive wicking material (not shown) that covers at least some of the perforations 26 and is also configured and dimensioned for disposing wicking material over approximately an exposed breadth of an opening in a person or an animal so that when the wicking material is so disposed by placement of the container 22, and a partial vacuum is applied at the outlet port 28, liquid can be drawn from the opening through the wicking material and the perforations 26 and into the chamber 14 and from the chamber 14 through the outlet port 28.

In this embodiment, it is preferable that the perforations 26 are arrayed on only a side of the container 22 that is configured to receive the wicking material.

In this embodiment, the container 22 has a flexible shell that can be shaped to fit the contours of the body of the person or animal and thereby enhance sealing of the container 22 to such body.

In both of the above described embodiments, it is preferable that the container has a flattened, but not flat, lateral profile, and that the container is hollow, as shown in FIG. 3, with there being only such interior structural supports as are necessary to keep the container from collapsing and/or such interior features as are necessary to accommodate manufacturing of the container. It is preferred that the container be flat enough to minimize the profile The container needs only enough height as to provide a chamber that can collect fluid and accommodate an outlet port that can be connected to tubing. In some examples, such height is in the range of about 0.5 cm to 1.0 cm. In other embodiments, the container has some other profile, such as elliptical.

To perform the method of drawing liquid from an opening in a body of a person or an animal by using a liquid collection device 10, 20, as described above at least some of the perforations 16, 26 are covered with wicking material; the container 12, 22 is so placed in, or over approximately an exposed breadth of, an opening in a body of a person or an animal that the wicking material is disposed in, or over approximately the exposed breadth of the, opening; and a partial vacuum is applied at the outlet port 18, 28 so that liquid is drawn from the opening through the wicking material and the perforations 16, 26 and into the chamber 14, and from the chamber 14 through the outlet port 18, 28.

The liquid collecting device 10, 20 can be used to collect and transport liquids, such as blood or exudate or irrigation fluid from wounds in the body of a person or an animal. The device 10 can be used to dispose the wicking material inside of deeper openings in the body, such as an abscess, or the bowels during a bowel surgery. For example, during an emergency laparotomy where blood and perhaps ruptured bowel with bowel contents are in the abdominal cavity, make viewing of the surgical site difficult, the use of the liquid collection device 10 will reduce the need for large numbers of sponges. If only blood is present in the wound (such as when there is a ruptured spleen or vessel), the blood can be collected by the liquid collection device 20 for re-transfusion back to the patient.

The device 20 can be used to dispose the wicking material over an exposed breadth of wounds to the outer surface of the body that are not deep.

The perforations 16, 26 in the container 12, 22 are naturally sealed when the container 12, 22 is placed against the body. The container 22 with the wicking material covering the perforations 26 in the container 22 of the liquid collection device 20 can be placed so that the wicking material is disposed over the exposed breadth of a wound at the surface of the body and held in place by such items as tape, bandages, a sock, a sleeve or a belt, thereby making dressing changes much easier, whereby such changes can then be done more frequently and thereby reduce the need for expensive skilled nursing services.

The liquid collection device 20 also is useful for removing unwanted liquid from an exposed portion of a body of a person or an animal when container 22 is configured and dimensioned for disposing wicking material over approximately the exposed breadth of a portion of the person or animal where unwanted liquid has accumulated, such as the eyes or under the breasts.

The container 12, 22 of the liquid collection device 10, 20 does not need to be pre-wetted with a liquid, such as Glycerin; the container 12, 22 does not have to be sealed, such as with Vaseline; the container 12, 22 does not have to have a hydrophilic membrane in contact with the body; and the container 12, 22 does not require that air not be able to pass through it in order for the device 10, 20 to function.

Other embodiments (not shown) of the liquid collection device of the invention can be used to collect fluid from a person's mouth during a dental procedure, or to collect unwanted liquid from the eyes of a person or animal.

The benefits specifically stated herein do not necessarily apply to every conceivable embodiment of the present invention. Further, such stated benefits of the present invention are only examples and should not be construed as the only benefits of the present invention.

While the above description contains many specificities, these specificities are not to be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. A method of drawing liquid from a wound opening in a body of a person or an animal, the method comprising:
   providing a liquid collection device that comprises: a hollow perforated container having an exterior surface and defining a chamber shaped to collect liquid drawn into the chamber through perforations in the exterior surface of the hollow perforated container, the exterior surface of the hollow perforated container being generally convex; wherein the hollow perforated container includes an outlet port through which liquid can be drawn from the chamber by a partial vacuum applied at the outlet port; wherein the hollow perforated container is configured to receive wicking material that covers at least some of the perforations and is also configured and dimensioned for placement of the wicking material in, or over approximately an exposed breadth of, a wound opening in a person or an animal, so that upon said placement of the hollow perforated container with at least some of the perforations being covered by said wicking material, when a partial vacuum is applied at the outlet port, liquid can be drawn from said wound opening through the wicking material and into the chamber and from the chamber through the outlet port, and wherein the hollow perforated container is flexible and configured to fit body contours of the person or the animal;

covering at least a portion of the exterior surface including at least some of the perforations with the wicking material;

at least partially immersing the hollow perforated container in the wound opening in the body of the person or the animal that the wicking material is disposed in; and applying a partial vacuum at the outlet port to cause liquid to be drawn from the opening through the wicking material and into the chamber and from the chamber through the outlet port, wherein the walls of the wound create a seal around the hollow perforated container, thereby enhancing the partial vacuum within the hollow perforated container.

2. The method according to claim 1, wherein when the hollow perforated container is configured and dimensioned for placement in said opening, providing the liquid collection device comprises providing said liquid collection device in which the perforations are arrayed around the hollow perforated container.

3. The method according to claim 1, wherein providing the liquid collection device comprises providing said liquid collection device in which the hollow perforated container has a flexible shell to enhance sealing of the hollow perforated container to said body.

4. The method according to claim 1, wherein at least partially immersing the hollow perforated container in the wound opening comprises:

during a surgery, disposing the hollow perforated container and the wicking material inside said wound opening where blood makes viewing of the surgical site difficult.

5. The method according to claim 1, wherein at least partially immersing the hollow perforated container in the wound opening comprises:

during a bowel surgery, disposing the hollow perforated container and the wicking material inside said wound opening where bowel contents make viewing of the surgical site difficult.

6. The method according to claim 1, further comprising:

holding the placed hollow perforated container in place by tape, bandages, a sock, a sleeve or a belt.

* * * * *